United States Patent [19]

Holmes

[11] 3,931,237

[45] Jan. 6, 1976

[54] PRODUCTION OF 2,2-DISUBSTITUTED PROPIOLACTONES

[75] Inventor: Jerry D. Holmes, Longview, Tex.

[73] Assignee: Eastman Kodak Company, Rochester, N.Y.

[22] Filed: July 23, 1974

[21] Appl. No.: 491,092

Related U.S. Application Data

[63] Continuation-in-part of Ser. No. 394,370, Sept. 4, 1973, abandoned.

[52] U.S. Cl. .............. 260/343.9; 252/454; 252/456
[51] Int. Cl.² ......................................... C07D 305/12
[58] Field of Search ................................. 260/343.9

[56] References Cited
UNITED STATES PATENTS

| | | | |
|---|---|---|---|
| 2,462,357 | 2/1949 | Caldwell et al. | 260/343.9 |
| 2,469,704 | 5/1949 | Stone | 260/343.9 |
| 2,806,064 | 9/1957 | McKlveen | 260/343.9 |
| 3,201,474 | 8/1965 | Hasek et al. | 260/343.9 |

Primary Examiner—Donald G. Daus
Assistant Examiner—Anne Marie T. Tighe
Attorney, Agent, or Firm—Edward R. Weber; Daniel B. Reece, III

[57] ABSTRACT

The present invention relates to a process for the manufacture of 2,2-disubstituted propiolactones from isoanhydrides and formaldehyde, as shown in the following equation:

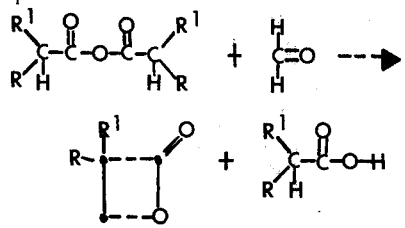

wherein R and $R^1$ individually may be a straight- or branched-chain alkyl, aryl or aralkyl group having 1 to 10 carbon atoms. The reaction is conducted at a temperature of from about 190°C. to about 400°C. in the presence of a metal oxide-silica gel complex which results from heating the calcined residue of a salt of a metal selected from the group consisting of Ta, Ti, Nb and Zr supported upon a silica gel in the presence of nitrogen and steam at a temperature of from about 650°C. to about 1000°C.

24 Claims, No Drawings

PRODUCTION OF 2,2-DISUBSTITUTED PROPIOLACTONES

This is a continuation-in-part application of my copending application, Ser. No. 394,370 filed Sept. 4, 1973 now abandoned, entitled "Production of 2,2-Disubstituted Propiolactones."

The present invention relates to a process for preparing 2,2-disubstituted propiolactones by the reaction of an isoanhydride with formaldehyde according to the following formula:

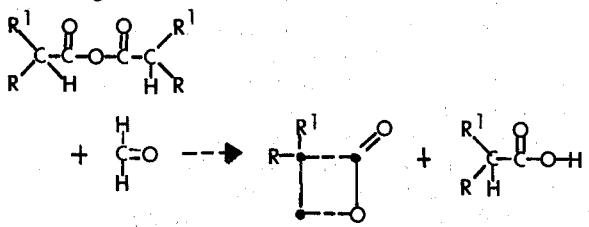

wherein R and $R^1$ individually may be a straight- or branched-chain alkyl, aryl, or aralkyl group having 1 to 10 carbon atoms, preferably 1 to 6 carbon atoms, at a temperature of from about 190°C. to about 400°C.

2,2-Disubstituted propiolactones are useful in the polymer industry as a starting material for synthetic resins and synthetic fibers. They are also useful in the pharmaceutical industry and have heretofore been prepared by a variety of methods. For example, in U.S. Pat. No. 2,356,459, there is described a well-known method for preparing 2,2-disubstituted propiolactones by the addition reaction of dimethyl ketene and formaldehyde. The known methods for the manufacture of 2,2-disubstituted propiolactones, however, can be practiced on the commercial scale only with difficulties and resultant economic disadvantages.

It is, therefore, an object of my invention to provide a simplified method for the preparation of 2,2-disubstituted propiolactones.

It is another object to provide a one-step method for the preparation of 2,2-disubstituted propiolactones.

Other objects of the invention will become apparent from a consideration of the sepcification and claims of this application.

The prior literature described a reaction of primarily aromatic aldehydes with anhydrides to give unsaturated acids. These reactions are normally conducted in the liquid phase using basic catalysts. Aliphatic aldehydes are usually unsuitable for this reaction. In the liquid phase, aldehydes normally react with anhydrides to form gem-diesters. For example, formaldehyde, when reacted with butyric anhydride, normally gives methylene dibutyrate (J. F. Walker, "Formaldehyde," 3rd Ed., ACS Monograph Series No. 152, Reinholt, p. 350). No prior literature is known which describes the condensation of aldehydes with acid anhydrides to produce lactones. U.S. Pat. application Ser. No. 303,567 filed Nov. 3, 1972, discloses a process for producing 2,2-disubstituted propiolactones from an isoanhydride and formaldehyde in the presence of a catalyst consisting of a supported heavy metal oxide. These catalysts, however, are not completely satisfactory because they give substantially lower yields and conversions of the desired lactone or they lose activity during use and are difficult to reactivate.

In the process of the instant invention, an isoanhydride having the formula

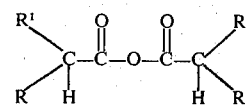

is condensed with formaldehyde to yield a 2,2-disubstituted propiolactone having the formula

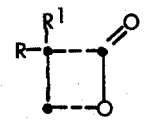

and an organic acid having the formula

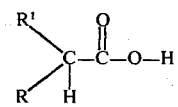

wherein R and $R^1$ individually may be a straight- or branched-chain alkyl, aryl or aralkyl group having 1 to 10 carbon atoms, preferably 1 to 6 carbon atoms. The reaction is catalyzed by a metal oxide-silica gel complex which results from heating the calcined residue of silica gel and a water-soluble salt of a metal selected from the group consisting of tantalum, titanium, niobium and zirconium in the presence of nitrogen and steam at a temperature of from about 650°C. to about 1000°C. and preferably less than about 900°C. Good results are obtained when the calcined residue is heated at a temperature of from about 730°C. to about 780°C. for a period of from about 3 to about 6 hours.

These catalysts give almost complete reaction of formaldehyde with isobutyric anhydride to form pivalolactone and, to a minor degree, a secondary reaction product, isobutyroxypivalic anhydride. This by-product appears to be formed from the secondary reaction of pivalolactone with isobutyric acid to form isobutyroxypivalic acid, which then interchanges with excess isobutyric anhydride as shown below.

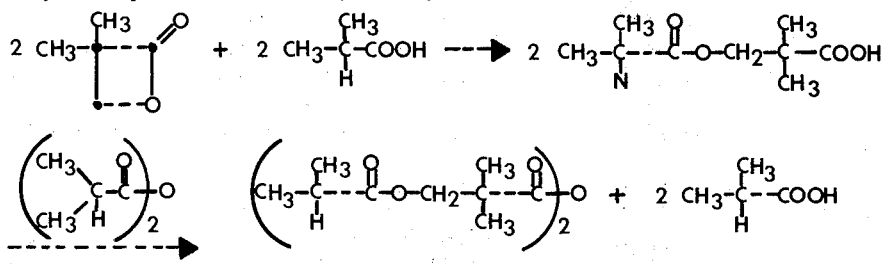

A common method of regeneration is to burn carbonaceous material from the catalyst at temperatures of up to about 550°C. The 550°C. temperature is selected since above about 600°C. silica gel begins to sinter and lose its structural properties. Since it had been determined that heating at 550°C. had very little effect on catalyst activity of the aforementioned heavy metal oxide catalyst (Ser. No. 303,567) it was quite surprising that heating a heavy metal oxide silica gel catalyst to temperatures of from about 650°C. to about 1000°C. produced a highly selective catalyst with long life which could be readily regenerated.

The supported metal oxide catalysts of the instant invention are conveniently formed by mixing one of their water-soluble salts such as a nitrate, acetate, oxalate, or ammonium salt with a silica gel and then removing the water by evaporation. Calcining the material in nitrogen at from about 400°C. to about 600°C. and then in air at from about 400°C. to about 600°C. produces the desired silica gel supported metal oxide. A preferred temperature range for the calcining steps is from about 500°C. to about 550°C. If desired, the metal oxide can be precipitated directly upon the support by use of a suitable chemical reaction. A relatively low surface area (340 square meters per gram) and large pore volume (1.15 cc. per gram) silica gel has been found to be particularly effective.

The silica gel supported calcined metal oxide is then heated in a nitrogen steam mixture at a temperature of from about 650°C. to 1000°C. until the desired metal oxide silica gel complex is formed, usually from about 2 to about 10 hours. The nitrogen is used to facilitate more uniform heat distribution. Good results have been obtained with $N_2$ to $H_2O$ ratios of from about 0.1:1 to about 10:1. An exact description of the catalyst complex is not available. It is best characterized by the unique, greatly improved properties it exhibits when compared to analogous catalysts or those prepared by alternate methods.

During the heat treating cycle (650°–1000°C.) the relationship of time of treatment to temperature may be varied considerably. Higher temperatures require shorter treatment times and vice versa. An excellent catalyst has been obtained by steam treatment in nitrogen at 760°–780°C. for 4 to 6 hours. It is essential, however, that the final heat treatment be in the 650°–1000°C. range. A more practical measurement to obtain a catalyst of greatest activity, selectivity and life span is based on the volume of the solid catalyst. When the catalyst being treated at 650°–1000°C. has been reduced in volume by not less than 5 percent and not more than 20 percent, the desired catalyst complex has been attained.

The importance of treatment at 650°–1000°C. is further described as follows. If insufficient heat treatment is used, the catalyst is too active and produces considerable decomposition resulting in low conversions and yields to lactones. On the other hand, if too much heat is applied the catalyst begins to lose activity which results in low conversions and a short lifetime.

In a preferred embodiment of the subject invention an aqueous solution of tantalum oxalate is used as a convenient source of soluble tantalum for the deposition of tantalum oxide on the silica gel. The catalyst is prepared by soaking the silica gel in an aqueous solution of the tantalum oxalate, removing the water by evaporation, calcining the solid residue in nitrogen at a temperature of about 550°C. for 1½ hours and then in air at a temperature of about 550°C. for 1½ hours, and heating the resultant silica gel-tantalum oxide mix in a nitrogen steam mixture at a temperature of from about 650°C. to about 1000°C. for 2 to 8 hours.

In an effort to ascertain the mechanism behind the improved catalyst performance and to ascertain if the high temperature treatment was simply reducing the activity of the silica gel, the catalyst was prepared by depositing tantalum oxide on a silica gel which had been previously heated at 760°C. to 780°C. in steam and nitrogen. This material gave much lower conversions and yields and had a relatively short catalyst life as compared to those obtained when the tantalum oxide and silica gel were exposed to the high temperature treatment together.

Optimum process conditions such as contact time, temperature, amount of diluent gas and feed composition will vary for the different metal oxide-silica gel complex catalysts. In general, the best results are obtained at a contact time of from about 0.5 to about 2.5 seconds, although this may vary over a much broader range, such as from about 0.1 second to about 5.0 seconds.

Preferably the temperature selected will be sufficient to insure vaporization of the reactants and the products. The process may be operated at temperatures of from about 190°C. to about 400°C. A preferred temperature range is from about 240°C. to about 300°C.

Suitable anhydrides include isobutyric, 2-ethylhexanoic, 2-phenylpropionic, 2-ethylpropionic, 2-ethylbutyric, and 2-methylpentanoic.

Formaldehyde may be fed as a gaseous monomer, as a trioxane solution, or as a paraformaldehyde slurry. It has been found that the aldehyde conversion to lactone is dependent on the amount of anhydride fed. A molar ratio of from about 1.15:1 to about 5:1, preferably from about 3:1 to about 4:1, of anhydride to formaldehyde (as trioxane) in the feed mixture produces good results. The optimum ratio will depend upon various manufacturing considerations, such as refining and recycling of unreacted feed materials. There appears to be no upper limit to this ratio other than practical manufacturing considerations which arise when a large excess of one material is introduced into a system. In general, a higher anhydride to formaldehyde ratio gives higher formaldehyde conversion, but also decreases the percentage of lactone in the product.

The reaction may be carried out at atmospheric, subatmospheric, or superatmospheric pressure. If desired, an inert diluent gas may be utilized to facilitate feeding of the reactants, control of contact time, etc. Good results are obtained at atmospheric pressure using an inert diluent gas, usually in a molar ratio of gas to organic feed of from about 1:10 to about 20:1, preferably about 1:1 to 6:1, and most preferably from about 2:1 to 4:1. A suitable inert diluent gas is any gas which does not react with either the reactants or the products under the conditions of the reaction, such as $N_2$, argon, helium, gaseous hydrocarbons and compounds which are readily vaporized such as benzene.

The process of the invention is illustrated in greater detail by the following examples which are all conducted at atmospheric pressure, but it will be understood that these examples are not intended to limit the invention in any way, and obvious modifications will occur to those skilled in the art.

EXAMPLE 1

This example illustrates a procedure for the preparation of my new and improved catalyst. To a 600 milliliter beaker is charged 60 milliliters of tantalum oxalate solution (10.32 grams as tantalum or 12.6 grams as tantalum oxide) and 240 milliliters water. To this is added 100 grams Davison G-59, 7–10 mesh silica gel and the mixture is left standing overnight. The mixture is transferred to a large evaporating dish and is taken to dryness on a steam bath. A small amount of powder is removed by collecting the catalyst on a 20 mesh screen.

To the usual Vycor reactor (30 millimeters by 2 feet) are charged 36 milliliters of Vycor chips, 150 milliliters (99 grams) of the above catalyst and 100 milliliters of Vycor chips for preheat. The reactor is brought to 550°C. with nitrogen and 8.18 moles per hour for approximately 1.5 hours and then air at 8.18 moles per hour is substituted for the nitrogen for an additional 1.5 hours. At this time the air is shut off and nitrogen at 8.18 moles per hour is again started. Water feeding is started through a preheater (approximately 100°C.) at a rate of about 180 milliliters per hour and the temperature is rapidly brought to 760°–780°C. and held for 6 hours. After the heat is shut off, steaming is continued until the reactor temperature decreases to about 550°C. at which point water feeding is discontinued. After cooling, the catalyst is removed from the reactor and has lost 14 percent of its original volume to a final value of 129 milliliters (60.4 grams).

EXAMPLE 2

The general procedure followed for testing all catalysts is described here. The reactor used is a 22 millimeter by 2 foot Vycor tube heated with a three-element furnace and charged with 35 milliliters Vycor chips, 50 milliliters catalyst and 90 milliliters Vycor chips for preheat. A nitrogen purge of 1.25 moles per hour is used and the feed rate is held at 60–61 milliliters per hour. The operating temperature is controlled at 256°–266°C. and a 3 to 1 molar ratio of isobutyric anhydride to formaldehyde (fed as trioxane) is used as feed. Gas liquid chromatography (4 foot column filled with 20M TPA Carbowax) is used to analyze the reaction product. A composite sample for each run is stripped at approximately 140°C. at 1–2 millimeters pressure to determine the percent high boilers (primarily isobutyroxypivalic anhydride). This is used to correct chromatograph results.

Following this procedure 50 milliliters of the catalyst from Example 1 is tested in continuous operation for four days. Formaldehyde conversion to pivalolactone averages 68 percent with 14 percent going to isobutyroxypivalic anhydride, the product derived from the secondary reaction between pivalolactone, isobutyric acid and isobutyric anhydride. Isobutyric anhydride yield averages 66 percent to pivalolactone and 20 percent to isobutyroxypivalic anhydride. This catalyst is then regenerated by burning clean in air and steam at 550°C. and put back into service. For a similar four day period formaldehyde conversion to pivalolactone averages 74 percent with 8 percent going to isobutyroxypivalic anhydride. Isobutyric anhydride yield averages 76 percent to pivalolactone and 12 percent to isobutyroxypivalic anhydride. Another similar regeneration cycle is carried out and essentially the same results are obtained.

EXAMPLE 3

This example shows the lower yields and conversions obtained by the usually prepared tantalum oxide on silica gel catalyst. The catalyst is prepared by the same procedure described in Example 1 except that after treatment in air at 550°C. for 1.5 hours the reactor is cooled and put into service. This material is not steam treated at high temperatures. The catalyst is tested as described in Example 2 in continuous operation for two days. For this period formaldehyde conversion to pivalolactone averages 28 percent with 26 percent going to isobutyroxypivalic anhydride. Isobutyric anhydride yield for the same two days averages 30 percent to pivalolactone and 41 percent to isobutyroxypivalic anhydride.

EXAMPLE 4

This example illustrates that steam treating the silica gel at high temperatures before adding tantalum oxide does not give a good catalyst. The catalyst is prepared by depositing tantalum oxalate on Davison G-59 silica gel (5.84 grams as tantalum on 52 grams silica gel) which has been treated in steam and nitrogen at 760°–780°C. for 6 hours. The tantalum oxalate is converted to tantalum oxide as usual by calcining at 550°C. in nitrogen and air. A typical run is made following procedures described in Example 2. Over a 24 hour period the following results are obtained. The formaldehyde conversion to pivalolactone and isobutyroxypivalic anhydride is 35 percent and 29 percent, respectively. For the same period the isobutyric anhydride yield is 34 percent to pivalolactone and 43 percent to isobutyroxypivalic anhydride. The percent unreacted formaldehyde in the product is up to 1.5 percent in the twenty-fourth hour showing a low catalyst life.

EXAMPLE 5

This example illustrates that our new and improved catalyst is effective for other disubstituted lactones. Using our new and improved catalyst as described in Example 1, the same procedures described in Example 2 are followed except that the feed mixture is a 3 to 1 molar ratio of 2-ethylhexanoic anhydride to formaldehyde (as trioxane). The formaldehyde conversion to $\alpha$-n-butyl-$\alpha$-ethylpropiolactone is 61 percent and the 2-ethylhexanoic anhydride yield to this lactone is approximately 50 percent.

EXAMPLE 6

This example shows that a usable catalyst may also be prepared by operating at higher temperatures. To a 4 liter beaker is charged 300 milliliters of tantalum oxalate solution (51.6 grams as tantalum or 63.0 grams as tantalum oxide) and 1.2 liters water. To this is added 500 grams Davison G-59 (3-8 mesh silica gel) and the mixture is left standing overnight. The mixture is transferred to a large evaporating dish and is taken to dryness on a steam bath. A small amount of fines is removed by collecting the catalyst on a 10 mesh screen.

To a Vycor reactor are charged 100 milliliters of inert ceramic packing, 300 milliliters of the above catalyst, and 600 milliliters of the ceramic packing for preheat. The reactor is brought to 500°–550°C. with nitrogen at 3 moles per hour and then air at 3 moles per hour is substituted for the nitrogen for approximatley 4 hours. The calcined catalyst is then cooled under nitrogen.

The nitrogen flow is increased to 4 moles per hour and the catalyst is heated to 865°–900°C. as rapidly as possible and held in this range for 6 hours. Water is fed through a preheater (85°–90°C.) at a rate of 300 milliliters per hour whenever the temperature exceeds 350°C. both during the heatup and cooldown periods. After cooling, the catalyst is removed from the reactor and has lost 17 percent of its original volume to a final value of 250 milliliters.

A 50 milliliter portion of this recovered catalyst is tested in continuous operation for 24 hours under the conditions outlined in Example 2. Formaldehyde conversion to pivalolactone averages 59 percent with 10 percent going to isobutyroxypivalic anhydride. Isobutyric anhydride yield for the same period averages 75 percent to pivalolactone and 20 percent to isobutyroxypivalic anhydride.

The invention has been described in detail with particular reference to preferred embodiments thereof, but it will be understood that variations and modifications can be effected within the spirit and scope of the invention as described hereinabove.

I claim:
1. A process for producing a 2,2-disubstituted propiolactone having the formula

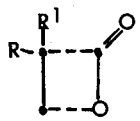

which comprises the steps of reacting an isoanhydride having the formula

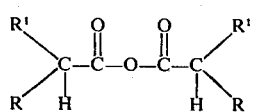

wherein R and $R^1$ individually may be straight- or branched-chain alkyl, having 1 to 10 carbon atoms, with formaldehyde or a formaldehyde yielding material at a temperature of from about 190°C. to about 400°C., in the presence of a catalyst consisting of the metal oxide-silica gel complex which results from heating the calcined residue of a mixture of silica gel and a water-soluble salt of a metal selected from the group consisting of tantalum, titanium, niobium and zirconium to a temperature of from about 650°C. to about 1000°C. in the presence of water vapor.

2. The process of claim 1 wherein each R and $R^1$ individually is straight- or branched-chain alkyl of 1 to 6 carbon atoms.

3. The process of claim 1 wherein the isoanhydride is selected from the group consisting of isobutyric anhydride, 2-ethylhexanoic anhydride, 2-phenylpropionic anhydride, 2-ethylbutyric anhydride, and 2-methylpentanoic anhydride.

4. The process of claim 1 wherein the catalyst is formed by mixing a water-soluble salt of the selected heavy metal with silica gel, removing the water by evaporation, and subsequently calcining the material at a temperature of from about 400°C. to about 600°C.

5. The process of claim 4 wherein the calcining takes place at a temperature of from about 500°C. to about 550°C.

6. The process of claim 1 wherein the calcined residue is heated, in the presence of water vapor, to a temperature of from about 730°C. to about 780°C.

7. The process of claim 6 wherein the calcined residue is heated, in the presence of water vapor, for a period of from about 3 to about 6 hours.

8. The process of claim 6 wherein the calcined residue is heated, in the presence of water vapor, to a temperature of from about 760°C. to about 780°C.

9. The process of claim 8 wherein the calcined residue is heated, in the presence of water vapor, for a period of from about 4 to about 6 hours.

10. The process of claim 1 wherein the reaction is conducted at a temperature of from about 240°C. to about 300°C.

11. The process of claim 1 wherein the process is conducted at atmospheric pressure.

12. The process of claim 1 wherein the ratio of anhydride to aldehyde is from about 1.15 to 1 to about 5 to 1.

13. The process of claim 12 wherein the ratio of anhydride to aldehyde is from about 3 to 1 to about 4 to 1.

14. A process for producing pivalolactone whereby isobutyric anhydride is reacted with formaldehyde at a temperature of from about 190°C. to about 400°C. in the presence of a catalyst consisting essentially of the metal oxide-silica gel complex which results from heating the calcined residue of a mixture of silica gel and a water-soluble salt of a metal selected from the group consisting of tantalum, titanium, niobium and zirconium to a temperature of from about 650°C. to about 1000°C. in the presence of water vapor.

15. The process of claim 14 wherein the catalyst is formed by mixing a water-soluble salt of the selected heavy metal with silica gel, removing the water by evaporation, and subsequently calcining the material at a temperature of from about 400°C. to about 550°C.

16. The process of claim 15 wherein the calcining takes place at a temperature of from about 500°C. to about 550°C.

17. The process of claim 14 wherein the calcined residue is heated, in the presence of water vapor, to a temperature of from about 730°C. to about 780°C.

18. The process of claim 17 wherein the calcined residue is heated, in the presence of water vapor, for a period of from about 3 to about 6 hours.

19. The process of claim 17 wherein the calcined residue is heated, in the presence of water vapor, to a temperature of from about 760°C. to about 780°C.

20. The process of claim 19 wherein the calcined residue is heated, in the presence of water vapor, for a period of from about 4 to about 6 hours.

21. The process of claim 14 wherein the reaction is conducted at a temperature of from about 240°C. to about 300°C.

22. The process of claim 14 wherein the reaction is conducted at atmospheric pressure.

23. The process of claim 14 wherein the ratio of anhydride fed to aldehyde is from about 1.15 to 1 to about 5 to 1.

24. The process of claim 23 wherein the ratio of anhydride fed to aldehyde is from about 3 to 1 to about 4 to 1.

* * * * *